United States Patent
Paulsen et al.

(10) Patent No.: US 12,239,494 B1
(45) Date of Patent: *Mar. 4, 2025

(54) HAND-HELD STEREOVISION SYSTEM FOR IMAGE UPDATING IN SURGERY

(71) Applicant: The Trustees of Dartmouth College, Hanover, NH (US)

(72) Inventors: Keith D. Paulsen, Lebanon, NH (US); Xiaoyao Fan, Hanover, NH (US); Songbai Ji, Hanover, NH (US); Sohail K. Mirza, Fairfax, VA (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,508

(22) Filed: Aug. 5, 2022

Related U.S. Application Data

(63) Continuation of application No. 16/595,377, filed on Oct. 7, 2019, now Pat. No. 11,406,471.

(60) Provisional application No. 62/742,313, filed on Oct. 6, 2018.

(51) Int. Cl.
| | |
|---|---|
| *H04N 13/239* | (2018.01) |
| *A61B 34/20* | (2016.01) |
| *A61B 90/00* | (2016.01) |
| *H04N 13/246* | (2018.01) |
| *A61B 90/50* | (2016.01) |

(52) U.S. Cl.
CPC ............ *A61B 90/361* (2016.02); *A61B 34/20* (2016.02); *H04N 13/239* (2018.05); *H04N 13/246* (2018.05); *A61B 2090/371* (2016.02); *A61B 2090/502* (2016.02)

(58) Field of Classification Search
CPC . A61B 90/361; A61B 34/20; A61B 2090/371; A61B 2090/502; H04N 13/239; H04N 13/246
See application file for complete search history.

(56) References Cited

U.S. PATENT DOCUMENTS

| 7,755,608 | B2 | 7/2010 | Chang | |
|---|---|---|---|---|
| 9,119,670 | B2 * | 9/2015 | Yang | A61B 5/055 |
| 11,406,471 | B1 * | 8/2022 | Paulsen | A61B 90/361 |

(Continued)

OTHER PUBLICATIONS

Lurie et al., "Effects of Viewing an Evidence-Based Video Decision Aid on Patients' Treatment Preferences for Spine Surgery", Spine (Phila Pa 1976). Aug. 15, 2011; 36(18): 1501-1504. doi:10.1097/BRS.0b013e3182055c1e.

(Continued)

*Primary Examiner* — Jeffery A Williams
*Assistant Examiner* — Tyler B Edwards
(74) *Attorney, Agent, or Firm* — Loginov & Associates, PLLC; William A. Loginov

(57) ABSTRACT

This invention provides a hand-held stereovision (HHS) system that is an efficient, accurate, and radiation-free imaging device to acquire intraoperative profiles of the exposed spine in prone position. The reconstructed intraoperative stereovision surfaces (iSV) are registered with preoperative CT (pCT; supine position) in a nonrigid fashion to generate updated CT images (uCT) and correct for vertebral posture and alignment changes. Updated CT images are uploaded to a commercial navigation system for surgical navigation.

14 Claims, 7 Drawing Sheets

(56) References Cited

U.S. PATENT DOCUMENTS

| | | | | |
|---|---|---|---|---|
| 2008/0135733 | A1* | 6/2008 | Feilkas | A61B 90/36 |
| | | | | 250/216 |
| 2014/0303491 | A1* | 10/2014 | Shekhar | G06T 7/337 |
| | | | | 600/424 |
| 2016/0191887 | A1* | 6/2016 | Casas | H04N 13/156 |
| | | | | 348/47 |
| 2016/0287211 | A1* | 10/2016 | DaCosta | A61B 8/48 |

OTHER PUBLICATIONS

Lurie et al., "Indications for spine surgery: validation of an administrative coding algorithm to classify degenerative diagnoses", Spine (Phila Pa 1976) Apr. 20, 2014, 39(9), 769-779.
Lurie et al., "Long-Term Outcomes of Lumbar Spinal Stenosis: Eight-Year Results of the Spine Patient Outcomes Research Trial (SPORT)", Spine (Phila Pa 1976). Jan. 15, 2015; 40(2): 63-76. doi:10.1097/BRS.0000000000000731.
Lurie et al., "Rates of Advanced Spinal Imaging and Spine Surgery", Spine vol. 28, No. 6, pp. 616-620, 2003.
Lurie et al., "Reliability of Readings of Magnetic Resonance Imaging Features of Lumbar Spinal Stenosis", Spine (Phila Pa 1976). Jun. 15, 2008; 33(14): 1605-1610. doi: 10.1097/BRS. 0b013e3181791af3.
Martin et al. "Hospital and Surgeon Variation in Complications and Repeat Surgery Following Incident Lumbar Fusion for Common Degenerative Diagnoses", Health Research and Educational Trust, DOI: 10.1111/.1475-6773.2012.01434.x , 26 pages.
Martin et al., "How Do Coverage Policies Influence Practice Patterns, Safety, and Cost of Initial Lumbar Fusion Surgery? A Population-based Comparison of Workers' Compensation Systems", Spine J. Jul. 1, 2014, 14(7), 1237-1246.
Martin et al., "Reoperation Rates Following Lumbar Spine Surgery and the Influence of Spinal Fusion Procedures", Spine vol. 32, No. 3, pp. 382-387, 2007.
Martin et al., "Repeat Surgery Following Lumbar Decompression for Herniated Disc: The Quality Implications of Hospital and Surgeon Variation", Spine J. Feb. 2012, 12(2), 89-97.
Martin et al., "Trends in Health Care Expenditures Utilization, and Health Status Among US Adults With Spine Problems, 1997-2006", Spine vol. 34, No. 19, pp. 2077-2084.
Martin, et al., "Expenditures and Health Status Among Adults with Back and Neck Problems", JAMA, Feb. 13, 2008, vol. 299, No. 6 (reprinted), pp. 656-664, downloaded from https://jamanetwork.com/ on Sep. 29, 2020.
Martin, et al., "Variation in the Care of Surgical Conditions: Spinal Stenosis", A Dartmouth Atlas of Health Care Series, The Dartmouth Institute, 2014 (c) Trustees of Dartmouth College, 48 pages.
McGuire et al., "The Effect of Extreme Obesity on Outcomes of Treatment for Lumbar Spinal Conditions: Subgroup Analysis of the Spine Patient Outcomes Research Trial (SPORT)", Spine (Phila Pa 1976). Nov. 1, 2014; 39(23): 1975-1980. doi:10.1097/BRS. 0000000000000577.
Mirza et al., "Accuracy of Thoracic Vertebral Body Screw Placement Using Standard Fluoroscopy, Fluoroscopic Image Guidance, and Computed Tomographic Image Guidance", Spine vol. 28, No. 4, pp. 402-413. 2003.
Mirza et al., "Developing a Toolkit for Comparing Safety in Spine Surgery", Instructional Course Lectures vol. 63, Apr. 2014, p. 271-286.
Mirza et al., "Development of an Index to Characterize the "Invasiveness" of Spine Surgery", Spine, vol. 33, No. 24, pp. 2651-2661, 2008.
Mirza et al., "Towards standardized measurement of adverse events in spine surgery: conceptual model and pilot evaluation", BioMed Central, BMC Musculoskeletal Disorders, 2006, 7:53, 16 pages.
Nandyala et al., "Minimally invasive transforaminal lumbar interbody fusion: one surgeon's learning curve", The Spine Journal 14 (2014) 1460-1465.
Nevzati et al., "Accuracy of Pedicle Screw Placement in the Thoracic and Lumbosacral Spine Using a Conventional Intraoperative Fluoroscopy-Guided Technique: A National Neurosurgical Education and Training Center Analysis of 1236 Consecutive Screws", World Neurosug. (2014) 82, 5:866-871.
Park et al., "Does Multilevel Lumbar Stenosis Lead to Poorer Outcomes? A Subanalysis of the SPORT Lumbar Stenosis Study", Spine (Phila Pa 1976). Feb. 15, 2010; 35(4): 439-446. doi:10.1097/BRS.0b013e3181bdafb9.
Patel et al., "Facet Violation With the Placement of Percutaneous Pedicle Screws", Spine vol. 36, No. 26, pp. E1749-E1752. 2011.
Pearson et al., "Predominant Leg Pain Is Associated With Better Surgical Outcomes in Degenerative Spondylolisthesis and Spinal Stenosis: Results from the Spine Patient Outcomes Research Trial (SPORT)", Spine (Phila Pa 1976). Feb. 1, 2011; 36(3): 219-229. doi:10.1097/BRS.0b013e3181d77c21.
Pearson et al., "Spine Patient Outcomes Research Trial", Spine vol. 33, No. 25, pp. 2759-2766. 2008.
Pearson et al., "Who should have surgery for spinal stenosis? Treatment Effect Predictors in SPORT", Spine (Phila Pa 1976). Oct. 1, 2012, 37(21), 1791-1802.
Pearson, et al., "Degenerative Spondylolisthesis Versus Spinal Stenosis", Spine 2010, vol. 35, No. 3, pp. 298-305.
Pfuntner, et al., "Most Frequent Procedures Performed in US Hospitals, 2011", HCUP, AHRQ, Statistical Brief #165, Oct. 2013, 10 pages.
Radcliff et al., "Does the duration of symptoms in patients with spinal stenosis and degenerative spondylolisthesis affect outcomes? Analysis of the Spine Outcomes Research Trial", Spine (Phila Pa 1976). Dec. 1, 2011, 36(25), 2197-2210.
Radcliff et al., "Epidural Steroid Injections Are Associated with Less Improvement in the Treatment of Lumbar Spinal Stenosis: A subgroup analysis of the SPORT", Spine (Phila Pa 1976). Feb. 15, 2013; 38(4): 279-291. doi:10.1097/BRS.0b013e31827ec51f.
Radcliff et al., "Risk for Adjacent Segment and Same Segment Reoperation After Surgery for Lumbar Stenosis: A subgroup analysis of the Spine Patient Outcomes Research Trial (SPORT)", Spine (Phila Pa 1976). Apr. 1, 2013; 38(7): 531-539. doi:10.1097/BRS. 0b013e31827c99f0.
Rajaee et al., "National trends in revision spinal fusion in the USA, Patient Characteristics and Complications", Bone Join J, 2014, 96-B:807-16.
Rajaee et al., "Spinal Fusion in the United States, Analysis of Trends from 1998 to 2008", Spine vol. 37, No. 1, pp. 67-76, 2012.
Rihn et al., "Does obesity affect outcomes of treatment for lumbar stenosis and degenerative spondylolisthesis? Analysis of the Spine Patient Outcomes Research Trial (SPORT)", Spine (Phila Pa 1976) Nov. 1, 2012, 37(23), 1933-1946.
Rihn et al., "Effectiveness of Surgery for Lumbar Stenosis and Degenerative Spondylolisthesis in the Octogenarian Population", J Bone Joint Surg Am, 2015, 97, 177-185.
Sagi, et al., "Electromagnetic Field-Based Image-Guided Spine Surgery Part One: Results of a Cadaveric Study Evaluating Lumbar Pedicle Screw Placement," Spine 2003 28(17) pp. 2013-2018.
Smorgick et al., "Single Versus Multilevel Fusion, For Single Level Degenerative Spondylolisthesis And Multilevel Lumbar Stenosis. Four-Year Results of the Spine Patient Outcomes Research Trial", Spine (Phila Pa 1976). May 1, 2013; 38(10): 797-805. doi: 10.1097/BRS.0b013e31827db30f.
Spitz et al., "Percutaneous "K-wireless" pedicle screw fixation technique: an evaluation of the initial experience of 100 screws with assessment of accuracy, radiation exposure, and procedure time", JNS Spine, J Neurosurg Spine 22: 422-431, 2015.
Tian, et al., "Pedicle screw insertion accuracy with different assisted methods: a systematic review and meta-analysis of comparative studies," Eur Spine J 2011 20 (6) 846-59.
Tjardes, et al., "Image-guided spine surgery: state of the art and future directions," Eur Spine J 2010 19 (1) 25-45.
Tosteson et al., "Comparative Effectiveness Evidence from the Spine Patient Outcomes Research Trial: Surgical vs. Non-Operative Care for Spinal Stenosis, Degenerative Spondylolisthesis and Intervertebral Disc Herniation", Spine (Phila Pa 1976) Nov. 15, 2011, 36(24), 2061-2068.

(56) References Cited

OTHER PUBLICATIONS

Tosteson et al., "Surgical Treatment of Spinal Stenosis with and without Degenerative Spondylolisthesis: Cost-Effectiveness after 2 Years", Ann Intern Med. Dec. 16, 2008; 149(12): 845-853.
Tow et al., "Does Navigation Improve Accuracy of Placement of Pedicle Screws in Single-level Lumbar Degenerative Spondylolisthesis? A Comparison O-Arm Navigation Techniques", Journal of Spinal disorders & Techniques, 28(8): E472-E477, Oct. 2015.
von Jako, et al., "Electromagnetic navigation for percutaneous guide-wire insertion: Accuracy and efficiency compared to conventional fluoroscopic guidance," Neuroimage 2009 47 Suppl 2 T127-32.
Walsh et al., "Is a Condition-Specific Instrument for Patients with Low Back Pain/Leg Symptoms Really Necessary? The Responsiveness of the Oswestry Disability Index, MODEMS, and the SF-36", Spine vol. 28, No. 6, pp. 607-615. 2003.
Wang et al., "Fusion techniques for adult isthmic spondylolisthesis: a systematic review", Arch Orthop Trauma Surg (2014) 134:777-784.
Weinstein et al., "Surgical versus Non-Operative Treatment for Lumbar Spinal Stenosis Four-Year Results of the Spine Patient Outcomes Research Trial (SPORT)", Spine (Phila Pa 1976). Jun. 15, 2010; 35(14): 1329-1338. doi: 10.1097/BRS.0b013e3181e0f04d.
Weinstein et al., "Surgical versus Nonsurgical Therapy for Lumbar Spinal Stenosis", N Engl J Med. Feb. 21, 2008; 358(8): 794-810. doi: 10.1056/NEJMoa0707136.
Weinstein, et al., "Surgical Compared with Nonoperative Treatment for Lumbar Degenerative Spondylolisthesis", Journal of Bone and Joint Surgery, Inc., 2009, pp. 1295-1304.
Weinstein, et al., "Surgical versus Nonsurgical Treatment for Lumbar Degenerative Spondylolisthesis", The New England Journal of Medicine, 2007, vol. 356, pp. 2257-2270.
Weinstein, et al., "United States' Trends and Regional Variations in Lumbar Spine Surgery: 1992-2003", Spine 2006, vol. 31, No. 23, pp. 2707-2714.
Yang et al., "Robot-Assisted Anterior Lumbar Interbody Fusion in a Swine Model In Vivo Test of the da Vinci Surgical- Assisted Spinal Surgery System", Spine vol. 36, No. 2, pp. E139-E143. 2011.
Abdu et al., "Degenerative Spondylolisthesis: Does Fusion Method Influence Outcome? Four-Year Results of the Spine Patient Outcomes Research Trial (SPORT)", Spine (Phila Pa 1976). Oct. 1, 2009; 34(21): 2351-2360. doi:10.1097/BRS.0b013e3181b8a829.
Allen et al., "Comparison Between Gearshift And Drill Techniques For Pedicle Screw Placement By Resident Surgeons", Int J Spine Surg 2015, vol. 9, article 23, DOI: 10.14444/2023, 6 pages.
Arega et al., "Racial Variation in Treatment Preferences and Willingness to Randomize in the Spine Patient Outcomes Research Trial (SPORT)", Spine (Phila Pa 1976). Sep. 1, 2006; 31(19): 2263-2269. doi: 10.1097/01.prs.0000232708.66608.ac.
Bao et al., "Fiducial markers configuration optimization in image-guided surgery", Bio-Medical Materials and Engineering 24(2014) 3361-3371.
Benzel, et al., "Complications in Spine Surgery: Honesty Is the Best Policy," World Neurosurg. Aug.-Sep. 2010; 74(2-3) 273-4.
Birkmeyer et al., "Design of the Spine Patient Outcomes Research Trial (SPORT)", Spine (Phila Pa 1976) Jun. 15, 2002, 27(12), 1361-1372.
Cai et al., "Automatic Geometric Rectification for Patient Registration in Image-guided Spinal Surgery", Proc of SPIE, vol. 9786, 10 pages. 2016.
Carreon, et al., "Perioperative Complications of Posterior Lumbar Decompression and Arthrodesis in Older Adults," JBJS 2003 85 A(11) 2089-92.
Cizik et al., "Using the Spine Surgical Invasiveness Index to Identify Risk of Surgical Site Infection, A Multivariate Analysis", J Bone Joint Surg Am, 2012, 94, 335-342.
Cummins et al., "Descriptive Epidemiology and Prior Healthcare Utilization of Patients in the Spine Patient Outcomes Research Trial's (SPORT) Three Observational Cohorts: Disc Herniation, Spinal Stenosis and Degenerative Spondylolisthesis", Spine (Phila Pa 1976) Apr. 1, 2006, 31(7), 806-814.
Desai et al., "Outcome Variation Across Centers After Surgery for Lumbar Stenosis and Degenerative Spondylolisthesis: The SPORT Experience", Spine (Phila Pa 1976). Apr. 15, 2013; 38(8): 678-691. doi:10.1097/BRS.0b013e318278e571.
Desai et al., "SPORT: Does incidental durotomy affect long-term outcomes in cases of Spinal Stenosis?" Neurosurgery. Mar. 2015; 76(01): S57-S63. doi: 10.1227/01.neu.0000462078.58454.14.
Desai et al., "SPORT: Does Incidental Durotomy Affect Long-term Outcomes in Cases of Spinal Stenosis?", Neurosurgery, 2011, 69(1) 38-44.
Desai et al., "Surgery for Lumbar Degenerative Spondylolisthesis in Spine Patient Outcomes Research Trial", Spine vol. 37, No. 5, pp. 406-413, 2012.
Deyo et al., "Back Pain Prevalence and Visit Rates, Estimates from US National Surveys, 2002", Spine vol. 31, No. 23, pp. 2724-2727.
Deyo et al., "Error in Trends, Major Medical Complications, and Charges Associated with Surgery for Lumbar Spinal Stenosis in Older Adults", JAMA, Sep. 14, 2011, vol. 306, No. 10.
Deyo et al., "Interspinous Spacers Compared to Decompression or Fusion for Lumbar Stenosis: Complications and Repeat Operations in the Medicare Population", Spine (Phila Pa 1976) May 1, 2013, 38(10), 15 pages.
Deyo et al., "Overtreating Chronic Back Pain: Time to Back Off?" J Am Board Fam Med. 2009, 22(1), 62-68.
Deyo et al., "Revision Surgery Following Operations for Lumbar Stenosis", J Bone Joint Surg Am, 2011, 93, 1979-1986.
Deyo et al., "Trends, Major Medical Complications, and Charges Associated with Surgery for Lumbar Spinal Stenosis In Older Adults", JAMA, Apr. 7, 2010, vol. 303, No. 13, pp. 1259-1265.
Deyo et al., "Use of Bone Morphogenetic Proteins in Spinal Fusion Surgery for Older Adults With Lumbar Stenosis", Spine vol. 37, No. 3, pp. 222-230. 2012.
Deyo, et al., "Trends and Variations in the Use of Spine Surgery", Clinical Orthopaedics and Related Research, No. 443, pp. 139-146, 2006.
Deyo, et al., "United States Trends in Lumbar Fusion Surgery for Degenerative Conditions", Spine 2005, vol. 30, No. 12, pp. 1441-1445.
Ershad et al., "Minimization of target registration error for vertebra in image-guided spine surgery", Int J Cars (2014) 9:29-38.
Fan et al., "Intraoperative fiducial-less patient registration using volumetric 3D ultrasound: a prospective series of 32 neurosurgical cases", J Neurosurg. Sep. 2015, 123(3): 721-731, DOI: 10.3171/2014.12.JNS141321.
Fritz et al., "The Associations Between Physical Therapy and Long-Term Outcomes for Individuals with Lumbar Spinal Stenosis in the SPORT study", Spine J. Aug. 1, 2014; 14(8): 1611-1621. doi:10.1016/j.spinee.2013.09.044.
Gelalis et al., "Accuracy of pedicle screw placement: a systematic review of prospective in vivo studies comparing free hand, fluoroscopy guidance and navigation techniques," Eur Spine J 2012 21(2) 247-55.
Gerard et al., "An analysis of tracking error in image-guided neurosurgery", Journal of the International Foundation for Computer Assisted Radiology and Surgery, vol. 10, No. 10, Oct. 2015, 1579-1588.
Ghobrial et al., "Iatrogenic neurologic deficit after lumbar spine surgery: A review", Clinical Neurology and Neurosurgery 139 (2015) 76-80.
Gill et al., "Biomechanically constrained groupwise ultrasound to CT registration of the lumbar spine", Medical Image Analysis 16 (2012) 662-674.
Hartov et al., "Adaptive spatial calibration of a 3D ultrasound system", 2010 American Association of Physicists in Medicine, DOI: 10.1118/1.3373520, Med. Phys. 37(5), pp. 2121-2130.
Holly, et al., "Image Guidance in Spine Surgery," Orthop Clin North Am 2007 38 (3) 451-61.
Holly, et al., "Intraoperative Spinal Navigation," Spine 2003, 28 (15 Suppl) 554-61.

(56) References Cited

OTHER PUBLICATIONS

Ji et al., "Combining Multiple True 3-D Ultrasound Image vols. through Re-registration and Rasterization", Med. Image Comput. Comput. Assist. Interv, Oct. 1, 2009, 12(Pt. 1), 795-802.

Ji et al., "Cortical surface shift estimation using stereovision and optical flow motion tracking via projection image registration", Medical Image Analysis 18 (2014) 1169-1183.

Ji et al., "Cortical Surface Strain Estimation Using Stereovision", Med Image Comput Comput Assist Interv. 2011 ; 14 (01):412-419.

Ji et al., "Efficient Stereo Image Geometrical Reconstruction at Arbitrary Camera Settings from a Single Calibration", Med Image Comput Comput Assist Interv. 2014, 17(01) pp. 440-447.

Ji et al., "Flow-Based Correspondence Matching in Stereovision", MLMI 2013, LNCS 8184, pp. 106-113, 2013.

Ji et al., "Intraoperative CT as a registration benchmark for intervertebral motion compensation in image-guided open spinal surgery", International Journal of Computer Assisted Radiology and Surgery, Jul. 2015, pp. 2009-2020.

Ji et al., "Intraoperative patient registration using volumetric true 3D ultrasound without fiducials", Med Phys 39(12), Dec. 2012, pp. 7540-7552.

Ji et al., "Mutual-information-based image to patient re-registration using intraoperative ultrasound in image-guided neurosurgery", Med. Phys. 35(10), Oct. 2008, pp. 4612-4624.

Ji et al., "Patient Registration Using Intraoperative Stereovision in Image-guided Open Spinal Surgery", IEEE Trans Biomed Eng. Sep. 2015; 62(9): 2177-2186. doi:10.1109/TBME.2015.2415731.

Ji et al., "Real-time Interpolation for True 3-Dimensional Ultrasound Image Volumes", J Ultrasound Med. Feb. 2011, 30(2), pp. 243-252.

John W. Frymoyer, MD, "Point of View", Spine 2005, vol. 30, No. 12, pp. 1446-1447.

Koivukangas et al., "Technical accuracy of optical and the electromagnetic tracking systems", SpringerPlus 2013, 2:90, 7 pages, http://www.springerplus.com/content/2/1/90.

Koreckij, et al., "Degenerative Spondylolisthesis", J. Spinal Disord Tech Aug. 2015; vol. 28, No. 7, pp. 236-241.

Krebs et al., "Predictors of long-term opioid use among patients with painful lumbar spine conditions", J Pain, Jan. 2010, 11(1), 15 pages.

Kurd et al., "Predictors of Treatment Choice in Lumbar Spinal Stenosis: A Sport Study", Spine (Phila Pa 1976). Sep. 1, 2012; 37(19): 1702-1707. doi:10.1097/BRS.0b013e3182541955.

Lee et al., "Risk Factors for Medical Complication After Lumbar Spine Surgery", Spine vol. 36, No. 21, pp. 1801-1806.

Lieberman et al., "Assessment of Pedicle Screw Placement Accuracy, Procedure Time, and Radiation Exposure Using a Miniature Robotic Guidance System", J Spinal Disord Tech, vol. 25, No. 5, Jul. 2012, www.jspinaldisorders.com, pp. 241-248.

* cited by examiner

HAND-HELD STEREOVISION SYSTEM FOR IMAGE UPDATING IN SURGERY

RELATED APPLICATION

This application is a continuation of co-pending U.S. patent application Ser. No. 16/595,377, entitled HAND-HELD STEREOVISION SYSTEM FOR IMAGE UPDATING IN SURGERY, filed Oct. 7, 2019, which claims the benefit of U.S. Provisional Application Ser. No. 62/742,313, entitled HAND-HELD STEREOVISION SYSTEM FOR IMAGE UPDATING IN SURGERY, filed Oct. 6, 2018, the entire disclosure of each of which applications is herein incorporated by reference.

FIELD OF THE INVENTION

This invention relates to hand-held devices for increasing the accuracy and effectiveness of surgical procedures such as lumbar fusion, and more particularly to camera-based devices.

BACKGROUND OF THE INVENTION

Posterior lumbar fusion with pedicle screw fixation leads to better bone healing and faster rehabilitation for patients with degenerative spondylolisthesis. However, suboptimally positioned pedicle screws can result in serious complications. It is desirable to provide a novel easy-to-use surgical navigation system to help surgeons place pedicle screws more accurately and safely in the lumbar spine. More generally, lumbar fusion is effective in reducing disability from symptomatic spondylolisthesis. Degenerative arthritis-related spine problems are associated with over $100 billion direct medical costs and 489,000 spinal fusion procedures each year. It is among the most common surgical procedures performed each year in the United States and rates of surgery are increasing. Fusion combined with decompression is effective for spondylolisthesis. Instrumented fusion is as effective as un-instrumented fusion for symptom relief, but since bone healing and spinal alignment is better with instrumented fusion, more than 90% of current fusion procedures involve instrumentation. Unfortunately, instrumentation is also associated with a higher complication rate. Most failures are related to fixation implants. Frequency of malpositioned pedicle screws is on average 9% (range 0.46% to 17%), potentially causing injury to nerve root, dura, or nearby vital structures, such as the aorta and vena cava.

Success of surgery depends on the surgeon's skill and experience, with wide variation in surgeon-level and hospital-level variation in complication rates. Accurate placement of screws within vertebral bone is critical to the success of these procedures. Technologies that assist the surgeon in precise, safe placement of fixation implants are likely to lead to fewer complications and faster recovery. Surgical navigation is promising in this regard, but time-consuming effort required to achieve adequate patient registration and adjust for intervertebral motion between the patient's supine position during preoperative scans and the prone position during surgery remain unsolved challenges in surgical navigation for spinal surgery. Spinal surgery studies have shown that use of image-guidance is associated with a decreased incidence in lumbar pedicle screw misplacement, compared to unaided free-hand surgery, especially when the navigation is based on computed tomography (CT) or three-dimensional (3D) fluoroscopy. However, current navigation methods are cumbersome to use and only marginally improve pedicle screw position. Unlike cranial neurosurgery, where skin-affixed fiducials are sufficient for registration, fiducials placed on the skin surface are not possible for registration in the spine because of the large registration errors that occur (up to 2 cm or even 3 cm in disk space location). Instead, spinal registration requires identification of anatomic landmarks within the surgical field, which involves a substantial effort on the part of the surgeon to define, expose, and localize the necessary features. In addition, the one-time registration at the start of surgery has not compensated for intervertebral motion resulting from a change in patient posture (supine during acquisition vs. prone during surgery) or intraoperative intervention, itself, which limits navigational accuracy, especially when multiple vertebrae are involved. Results are underwhelming for systems that use preoperative computed tomography (CT) scans, intraoperative fluoroscopic images for a pseudo-CT, or robotics. Not surprisingly, navigation has not been widely adopted in spinal surgery.

Prior art automated methods use intra-operative CT, exposing both the patient and the surgical team to significant ionizing radiation. Also, substantial capital costs are significant concerns and practical barriers to wide deployment. Two-dimensional (2D) and 3D fluoroscopy is more limited compared to intraoperative CT, and even though the radiation dose may be reduced, the guidance information relative to any preoperative high-resolution scans is suboptimal. Thus, image-guided spine procedures would benefit substantially from a more practical and efficient patient registration approach, especially if the technique could also compensate for intervertebral motion that occurs at the start and during the case.

A practical, efficient and accurate registration approach is needed to lower the technical complication rates. More particularly, it is desirable to provide a novel surgical navigation technology to improve accurate placement of pedicle screws in patients with degenerative spondylolisthesis. Improving surgeon proficiency could have a powerful impact in terms of reducing surgical-skill dependent complications and improving outcomes for the large population of patients receiving surgery each year for this diagnosis.

SUMMARY OF THE INVENTION

This invention overcomes disadvantages of the prior art by providing a hand-held stereovision (HHS) system that is an efficient, accurate, and radiation-free imaging device to acquire intraoperative profiles of the exposed spine in prone position. The reconstructed intraoperative stereovision surfaces (iSV) are registered with preoperative CT (pCT; supine position) in a nonrigid fashion to generate updated CT images (uCT) and correct for vertebral posture and alignment changes. Updated CT images are uploaded to a commercial navigation system for surgical navigation.

In an exemplary embodiment, a stereoscopic vision system for use in surgery procedures can include a handheld stereovision device, the HHS including a body, at least two cameras mounted to the body, the at least two cameras angled towards a center of a field of view, and having an overlapping region of view; a surgical tracker, and a data connection. The stereoscopic vision system can include a processor operatively connected to the handheld stereovision device through the data connection, the processor including an image data gathering module, and a tracking data gathering module. The stereoscopic vision system can include an iSV reconstruction module. The stereoscopic vision system can include a patient registration module. The stereoscopic vision system can include a surgical navigation system. The stereoscopic vision system can include an external monitor display system or heads-up display within the surgeon's field of view.

In an exemplary embodiment, a method of performing surgery using a handheld stereovision system can include obtaining a handheld stereovision (HHS) device, the HHS device including at least two cameras and a surgical tracker; gathering image information from the two or more cameras and location data from the surgical tracker at the same time; reconstructing iSV images; registering patient data; uploading uCT images to a surgical navigation system; and performing a surgery in a surgery treatment area using the uCT images with the surgical navigation system. The method can include calibrating stereo images; and calibrating spatial images. The surgery treatment area can be a lumbar region of the vertebra. The method can include moving the HHS by hand over the surgery treatment area to increase a size of an area being analyzed for surgery.

In an exemplary embodiment, an apparatus for using data from a handheld stereoscopic (HHS) device to assist with surgery can include a computer system; a computer code in the computer system, the computer code including a method for gathering image information from two or more cameras on the HHS; a method for gathering location information from a tracker on the HHS; a method for reconstructing iSV images; a method for registering patient data; and a method for uploading uCT images to a surgical navigation system. The computer code can include a method for displaying the uCT images to a surgeon during surgery to improve surgical outcomes. The computer code can include a method of calibrating stereo images and a method of calibrating spatial images.

BRIEF DESCRIPTION OF THE DRAWINGS

The invention description below refers to the accompanying drawings, of which.

DETAILED DESCRIPTION

I. System Overview and Usage

A hand-held stereovision (HHS) system can be an efficient, accurate, and radiation-free imaging device to acquire intraoperative profiles of the exposed spine in prone position. The reconstructed intraoperative stereovision surfaces (iSV) can be registered with preoperative CT (pCT; supine position) in a nonrigid fashion to generate updated CT images (uCT) and correct for vertebral posture and alignment changes. Updated CT images can be uploaded to a commercial navigation system for surgical navigation.

Figures 1A, 1B:
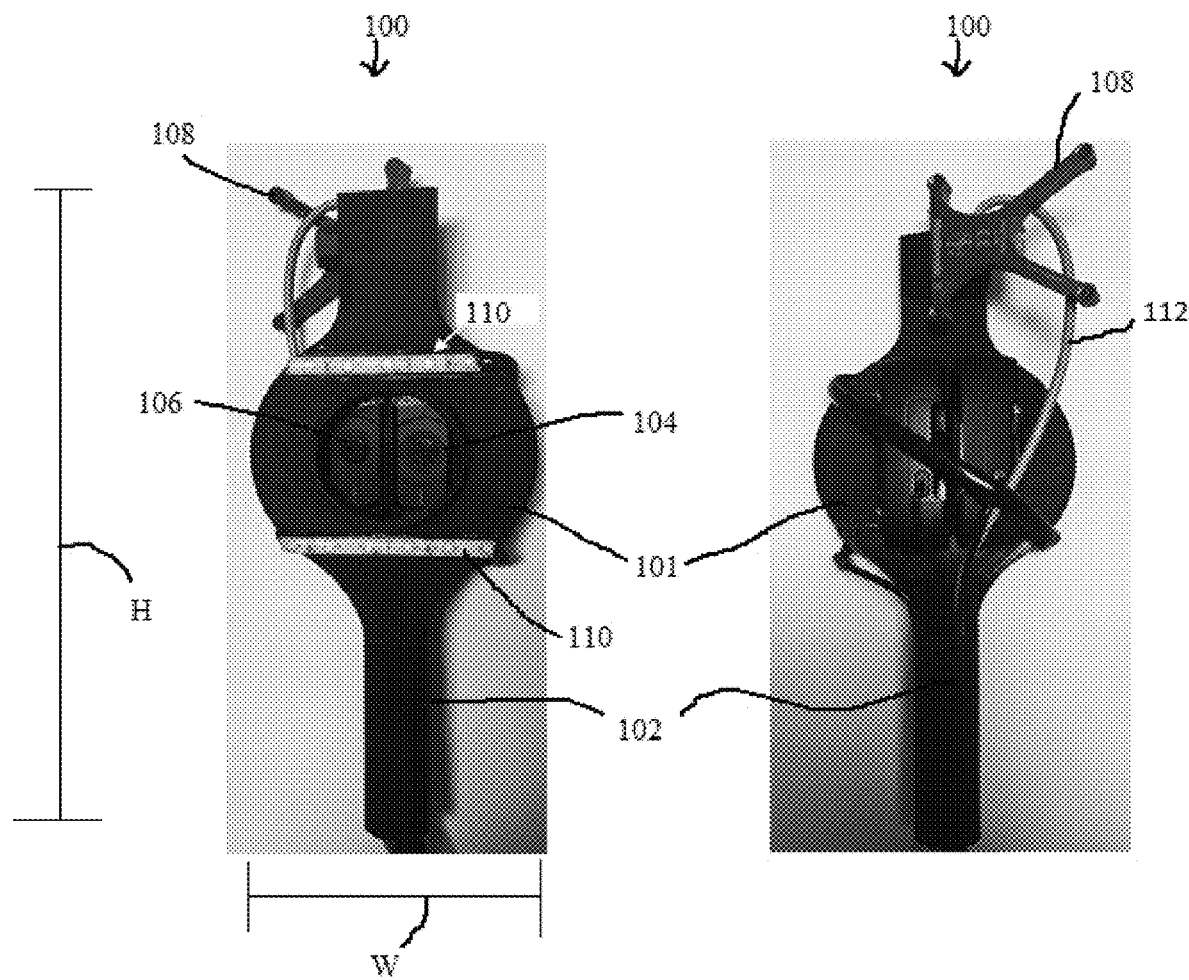
FIG. 1A is a front view of an exemplary hand-held stereovision device (HHS) for use with the system and method herein, according to an illustrative embodiment.
FIG. 1B is a rear view of an exemplary (HHS) for use with the system and method herein, according to an illustrative embodiment.

FIG. 1A is a front view of an exemplary hand-held stereovision device, and FIG. 1B is a rear view of an exemplary hand-held stereovision device for use with the system and method herein, according to an illustrative embodiment. An HHS 100 can include a body 101 with a handle 102. In various embodiments, the body 101 with handle 102 can be 3D printed and can be made from polylactic acid (PLA). In various embodiments, the body 101 can be adapted for head-mounted use, so that a surgeon can mount the HHS on his head.

The HHS 100 can have two or more cameras. In an embodiment, the HHS can have a left camera 104 and a right camera 106. The left camera 104 and right camera 106 can be arranged on opposing sides of the handle's central axis. The cameras can be High Definition (HD) cameras, such as, for example, model C920 from Logitech in Lausanne, Switzerland. The cameras are described herein as a left camera and a right camera, however, it should be clear that the cameras can be arranged in various different orientations, such as one over the other in a top and bottom arrangement, or other various arrangements that will be clear to one skilled in the art.

For simplicity, the HHS is described herein as having two cameras, however, three or more cameras are possible. In various embodiments, an HHS can include three cameras, which can increase the field of view and thus reduce the number of iSV image acquisitions necessary; and can enhance the robustness in stereovision correspondence matching (three pairs of corresponding matching vs. one pair in the previous 2-camera system), which can improve the accuracy of the reconstructed iSV surface.

An active tracker 108 can be rigidly attached to the HHS, such as the active tracker manufactured by Medtronic in Louisville, Colorado. The active tracker 108 can allow the location of the HHS device to be tracked in three dimensions and in real time during surgery. The HHS can have one or more light sources 110 that can be, by way of non-limiting example, Ustellar LED adjustable strip lights manufactured by Ustellar in Shenzhen, China. In an exemplary embodiment the HHS can have a height H from top to bottom of approximately 31 cm, a width W from side to side of approximately 11 cm, and a depth from front to back of approximately 5 cm.

The two cameras 104 and 106 can be angled towards the center of field of view (FOV), and the overlapping region can be maximized at a distance of 15 cm (distance from HHS to surgical field). The camera attributes can be adjustable using National Instruments Measurement & Automation Explorer (MAX) software. Some attributes are tied to camera calibration, including image size, focal value, and zoom. The settings can be changed, and a new calibration needs to be performed when any of the 3 settings is changed. In one exemplary configuration, the image resolution can be 1920×1080 pixels for each camera with a frame rate of 30 frames per second (fps). The focus value can be set to 15 on each camera, zoom factor at the lowest, and all settings can be configured to be the same for both cameras. The HHS can have a data connection 112 that can provide image data from the cameras to a processor, and the data connection can be wired or wireless.

A. Data Acquisition

Figure 2:
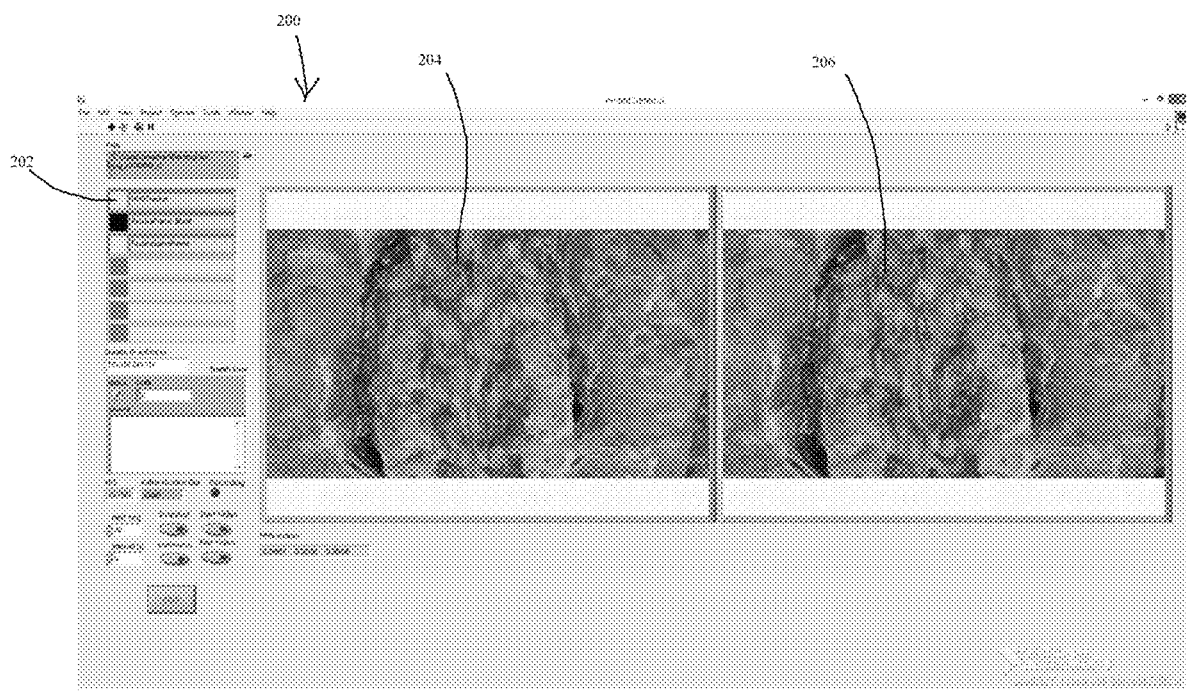
FIG. 2 is a screen image of an exemplary software application display used to obtain and store image and tracking data, according to an illustrative embodiment.

FIG. 2 is a screen image of an exemplary software application display used to obtain and store image and tracking data, according to an illustrative embodiment. Image data can be gathered from the two or more cameras, and tracking data can be gathered from the tracker on the HHS. Tracking information can be obtained from a commercial navigation system, such as, for example, the StealthStation S7, from Medtronic, in Louisville, Colorado through the StealthLink from Medtronic, in Louisville, Colorado. Image data and tracking data can be acquired using, for example, Labview from National Instruments, in Austin, TX and MATLAB from MathWorks, in Natick, MA. As shown in FIG. 2, a Labview interface 200 termed virtual instruments (VI) can facilitate data acquisition. An instrument panel 202 can indicate the visibility of 3 instruments in the StealthStation. An instrument of interest needs to be green to ensure accuracy of tracking data. The interface 200 can have two image panels including a left image panel 204 and a right image panel 206. The two image panels 204 and 206 can show real-time images from the left and right cameras 104 and 106. Movement of the HHS tracker can be measured at the time of data acquisition for each image pair to indicate the potential error due to hand motion.

B. Calibration

Calibration of the HHS can include two components. Stereo calibration can obtain stereo parameters for reconstruction of the 3D iSV surface, and spatial calibration can obtain the location of iSV surface in the StealthStation (tracking device) coordinate system. Calibration of a two-camera system is described herein, however, it should be clear that calibration of a system with three or more cameras is also possible.

The same calibration target (e.g. a checkerboard pattern with 6×7 black and white 20 mm squares) can be used for both components of calibration. A calibration target such as a checkerboard can be printed on a piece of paper and fixed onto a flat surface. A reference frame such as a spine frame from Medtronic in Louisville, Colorado can be rigidly attached to the checkerboard at the beginning of calibration. Multiple image pairs can be acquired from various angles, orientations, and locations, with the checkerboard pattern fully visible in both images of each image pair. With the spine frame and HHS tracker both visible in the collected image pairs, their locations in the physical space can be acquired. By way of non-limiting example, their locations in the physical space can be well-acquired through the collection of approximately 42 image pairs.

B(1). Stereo Calibration

Figure 3:
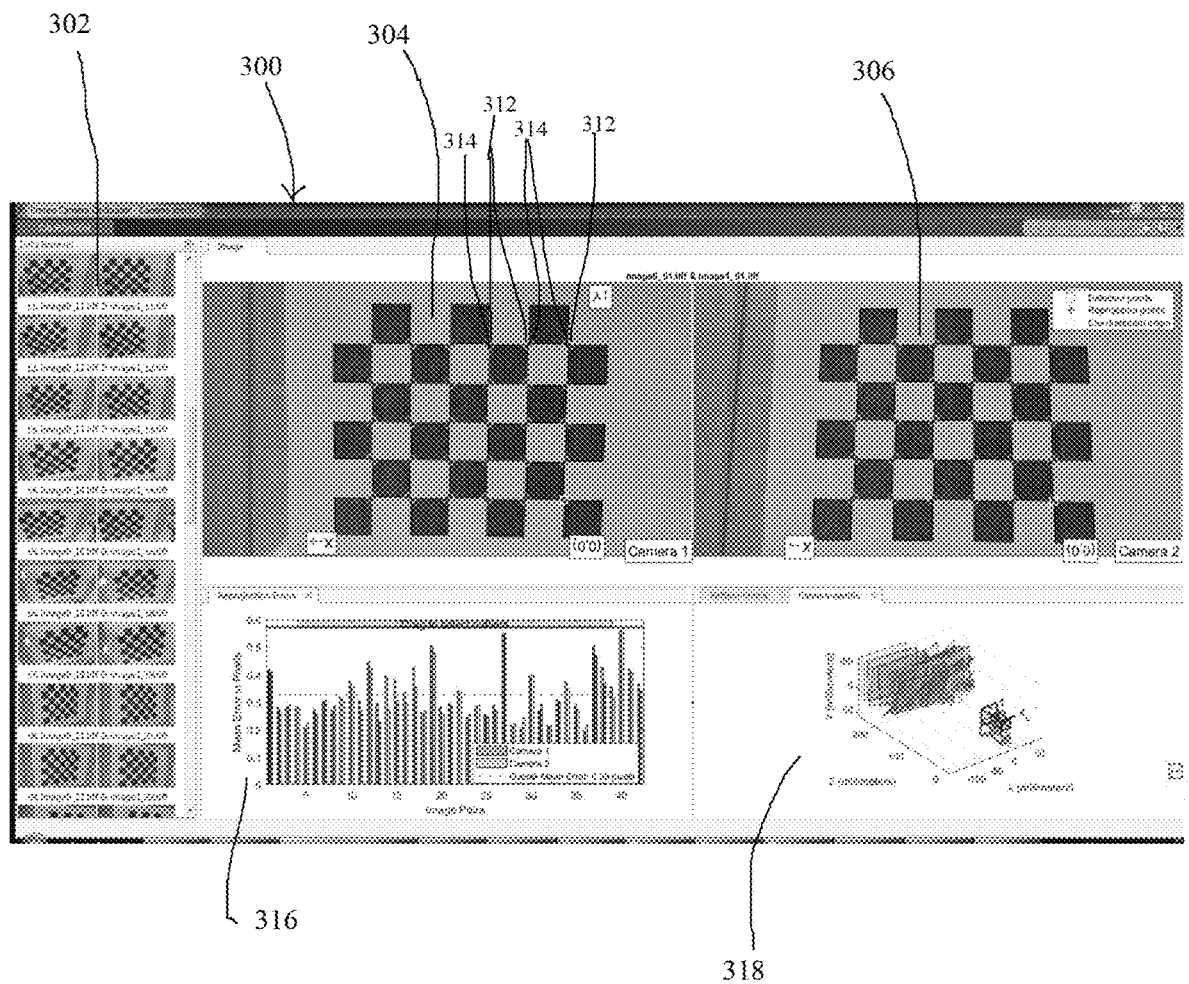
FIG. 3 is a diagram of an exemplary stereo camera calibration in the software application MATLAB, according to an illustrative embodiment.

Stereo calibration can be performed using the Stereo Camera Calibrator in MATLAB from MathWorks, in Natick, MA. FIG. 3 is a diagram of an exemplary stereo camera calibration in the software application MATLAB, according to an illustrative embodiment. As depicted in FIG. 3, the screen 300 shows the collected image pairs that can be used for calibration are shown in the collected image column 302. Each image pair in the column includes the left side and the right side image that have been taken from the two cameras 104 and 106 at the same time and the same tracked position of the HHS. A selected image pair can be shown in the left and right stereo image calibration panels 304 and 306. The circles 312 in each image show detected points from the image, and crosses 314 show reprojected points. In the example shown in FIG. 3, two-point sets are well aligned with the crosses within the circles, indicating a favorable accuracy. The bottom left data display 316 shows the mean error in pixels for each image pair, and the bottom right data display 318 shows the various locations and orientations of image pairs acquired with respect to the HHS.

B(2). Spatial Calibration

Spatial calibration is performed by tracking square corners from the checkerboard (using the same points as used in stereo calibration) in both camera space and StealthStation (tracking device) space. The tracking device on the StealthStation can be, by way of non-limiting example, the "Polaris" tracking device made by Northern Digital Inc, in Waterloo, Ontario, Canada, and throughout the following text herein, the tracking device will be referred to as "Polaris."

For spatial calibration, digitized intersections of squares on the checkerboard (30 points) are digitized using a tracked stylus (Medtronic, Louisville, Colorado). The locations of these points in the frame space are:

$$p_{frame} = {}^{frame}T_{Polaris} \times {}^{Polaris}T_{probe} \times p_{probe\ tip} \qquad (1)$$

For a particular image pair, the stylus-tracked points in HHS tracker space are:

$$p_{HHStracker} = \text{inv}({}^{Polaris}T_{HHS\ tracker}) \times \text{inv}({}^{Frame}T_{Polaris}) \times {}^{Frame}T_{Polaris} \times {}^{Polaris}T_{Probe} \times p_{probe\ tip} \qquad (2)$$

Then, the 30 square corners can be reconstructed in each of the image pairs. Specifically, for each image pair, the left and right images can be rectified using stereo parameters obtained through stereo calibration to generate left and right rectified images. Square corners are detected from left and right rectified images, and their 3D coordinates (x, y, z) can be calculated using stereo parameters obtained through stereo calibration. These 3D points are in the camera space ($P_{Camera}$). In some images, the detected points can be inaccurate, and thus the reconstructed 3D points are inaccurate and need to be excluded. In the rectified images, the same features should appear along the same horizontal line, i.e., the y coordinates of the same square corner in the left and right rectified images should be the same. This assumption can be used to exclude points due to inaccurate point detection.

The corresponding reconstructed locations of square corners in the frame space are:

$$p'_{frame} = {}^{frame}T_{Polaris} \times {}^{Polaris}T_{HHS\ tracker} \times {}^{HHS\ Tracker}T_{Camera} \times p_{Camera} \qquad (3)$$

Their locations in the HHS tracker are:

$$p'_{HHS\ Tracker} = {}^{HHS\ tracker}T_{Camera} \times p_{Camera} \qquad (4)$$

A transformation ${}^{HHS\ tracker}T_{Camera}$ can then be calculated to minimize the distance between tracked points $p_{HHS\ Tracker}$ and reconstructed points $p'_{HHS\ Tracker}$.

Figure 4:
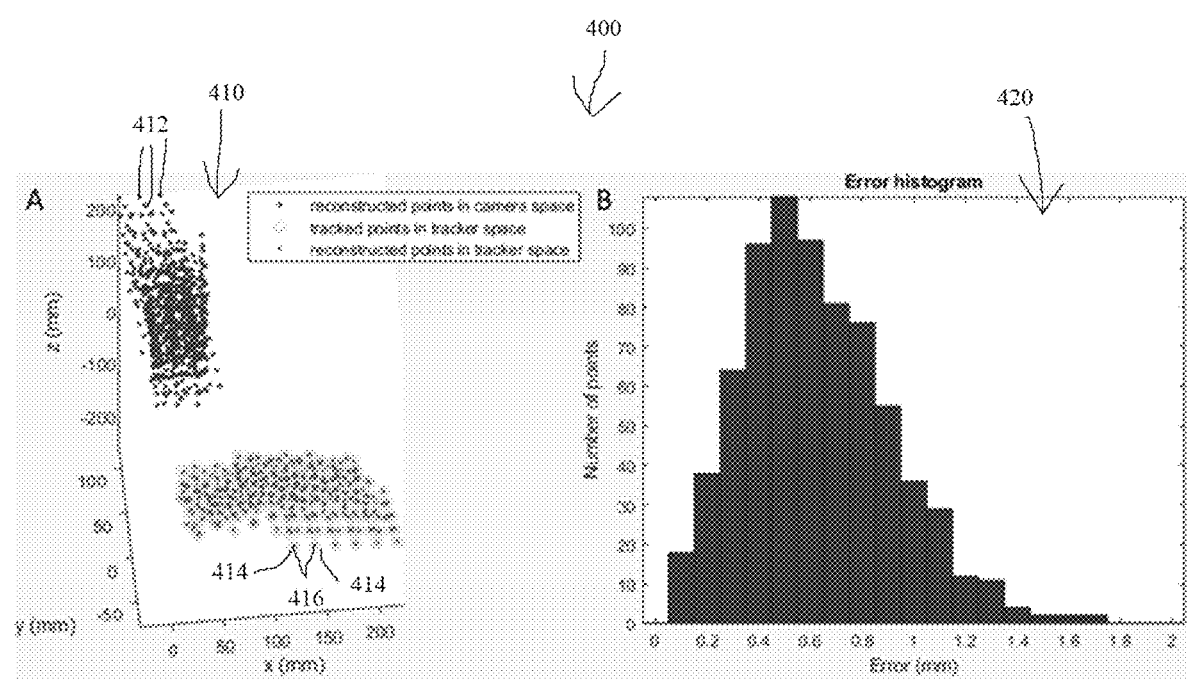
FIG. 4 is a diagram showing spatial calibration according to an illustrative embodiment of the system and method.

Spatial calibration is shown in the screen depiction 400 of FIG. 4. The left data display 410 shows reconstructed points in camera space as dots 412, tracked points in tracker space as circles 414, and reconstructed points transformed into tracker space as dots 416. The right data display 420 shows a histogram of errors from each point.

The results of an exemplary spatial calibration are shown in FIG. 4. The reconstructed points matched well with tracked points in tracker space, and the overall error was 0.63±0.29 mm using a total of 731 points.

C. iSV Reconstruction

The Labview VI shown in FIG. 2 can be used for data acquisition in surgical cases. For each new image pair, an iSV surface can be reconstructed in the following steps:
1. Image rectification.
2. Stereo correspondence computation using an optical flow based algorithm to obtain disparity map in the horizontal direction.

3. Reconstruction of the 3D surface using stereo parameters obtained from stereo calibration.
4. Transform the reconstructed 3D surface from camera space to StealthStation space, using transformation obtained from spatial calibration.

Figure 5:
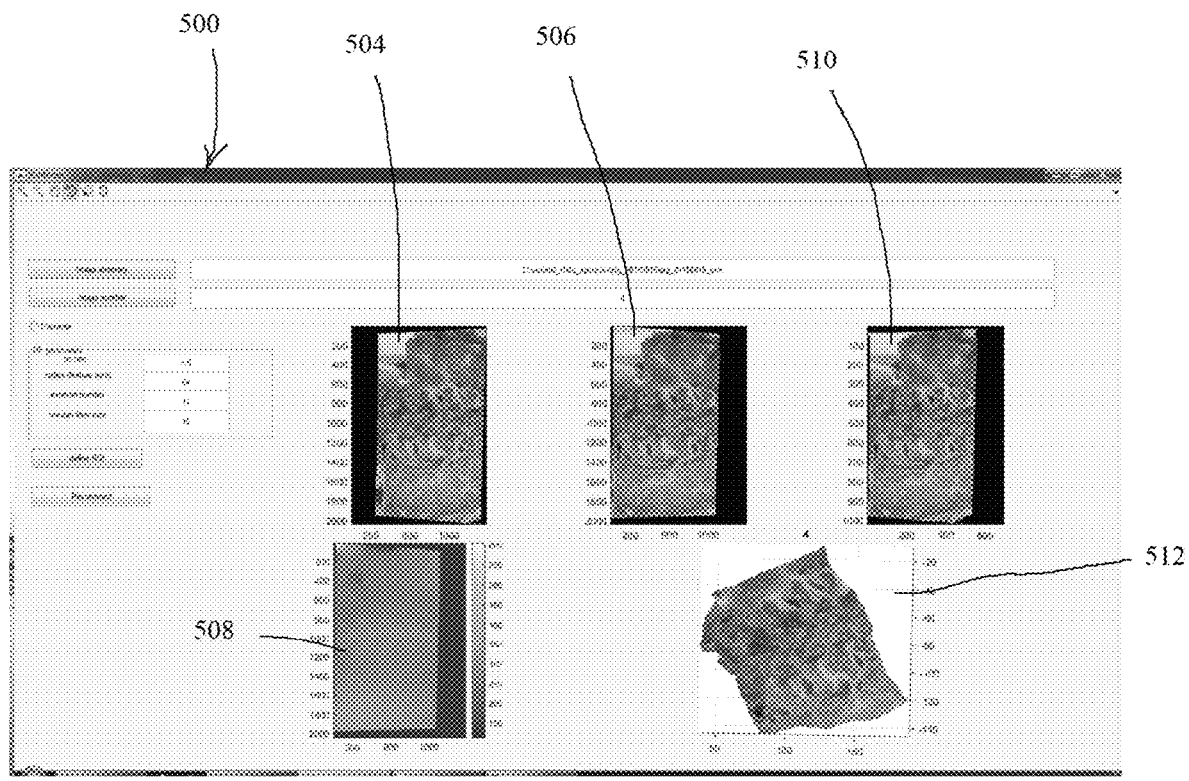
FIG. 5 is an exemplary graphical user interface (GUI) screen designed to process iSV data in the system and method.

FIG. 5 shows an exemplary graphical user interface (GUI) 500 designed to process iSV data. The left rectified image 504 shows the rectified image from the left camera 104, and the right rectified image 506 shows the rectified image from the right camera 106. The disparity map 508 shows the disparity in x direction (horizontal disparity) which indicates the depth of each pixel. The disparity map 508 is used to deform the left rectified image and generate a warped image 510. The similarity between the warped image 510 and original right rectified image 506 provides a visual feedback of the validity of the disparity map 508. The iSV surface can then be reconstructed, and the final reconstructed iSV is shown in the panel reconstructed iSV panel 512.

D. Patient Registration

Patient registration can include the following components:
1. Automatic geometric rectification of spine extracted from pCT
2. Automatic geometric rectification of spine extracted from iSV
3. Project rectified spines from pCT and iSV onto 2D plane to generate depth maps.
4. A refined registration is achieved using an iterative closest point (ICP) algorithm.
5. A level-wise registration between each level in pCT and iSV to compensate for intervertebral motion.
6. Deformation of pCT to produce uCT.
7. Upload uCT to StealthStaion for surgical navigation.

E. System Overview

Figure 6:
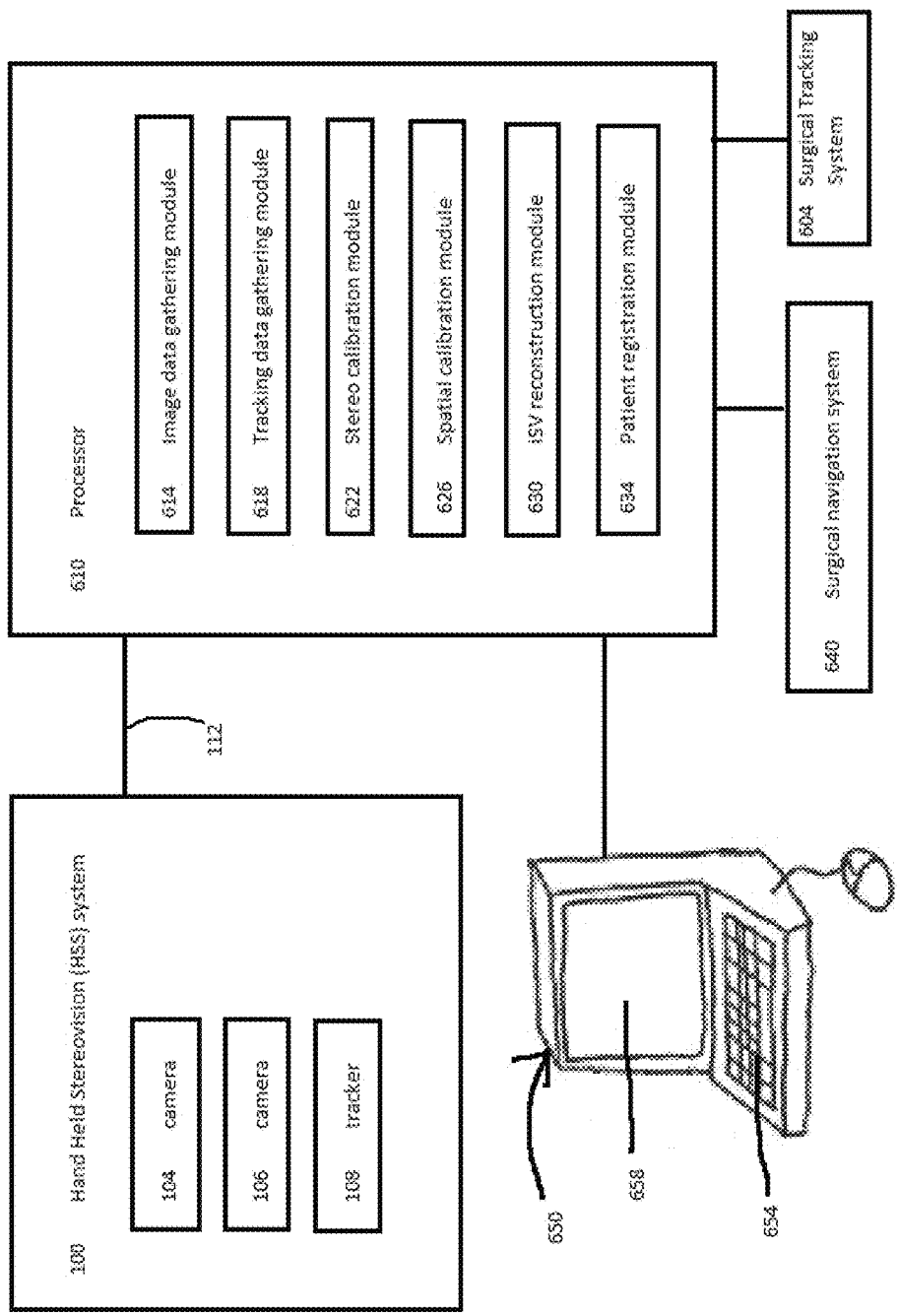
FIG. 6 is a schematic diagram of an exemplary system for use with a hand-held stereovision system for image updating in surgery, according to an illustrative embodiment.

FIG. 6 is a schematic diagram of an exemplary system for use with a hand-held stereovision system for image updating in surgery. An imaging system 600 includes a hand-held stereovision device (HHS) 100 that includes a tracker 108 and at least two cameras 104 and 106. The imaging system 600 includes a processor 610 with an image data gathering module 614 that can gather image data from the two or more cameras 104 and 106, and a tracking data gathering module 618 that can gather location tracking data from the tracker 108. The system 600 can include a data connection 122 that can allow the processor 610 to receive image data from the HHS. The system 600 can include a surgical tracking system 604 that can track the physical location of the tracker 108 as it moves through space. The processor 610 can include a stereo calibration module 622 that can calibrate the images from the two or more cameras 104, 106. The processor 610 can include a spatial calibration module 626 that can rectify the stereo calibrated images with the 3D points in the camera space. The processor can include an iSV reconstruction module 630 that can reconstruct an iSV surface. The processor 610 can include a patient registration module 634 that can register iSV surfaces with pCT to generate uCT images that can be uploaded to a commercial navigation system 640 for surgical navigation.

The processor 610 can be operatively connected to the surgical navigation system 640, so that the uCT images can be used to guide and inform a surgeon in surgery in order to provide significant improvement in surgical outcomes. The processor 610 can be contained within a general purpose, or dedicated, computing device 650, such as a PC, laptop, tablet or smartphone. The computing device 650 can include a user interface that can be a keyboard, touch screen or similar device 654, and a display 658.

F. Method Overview

Figure 7:
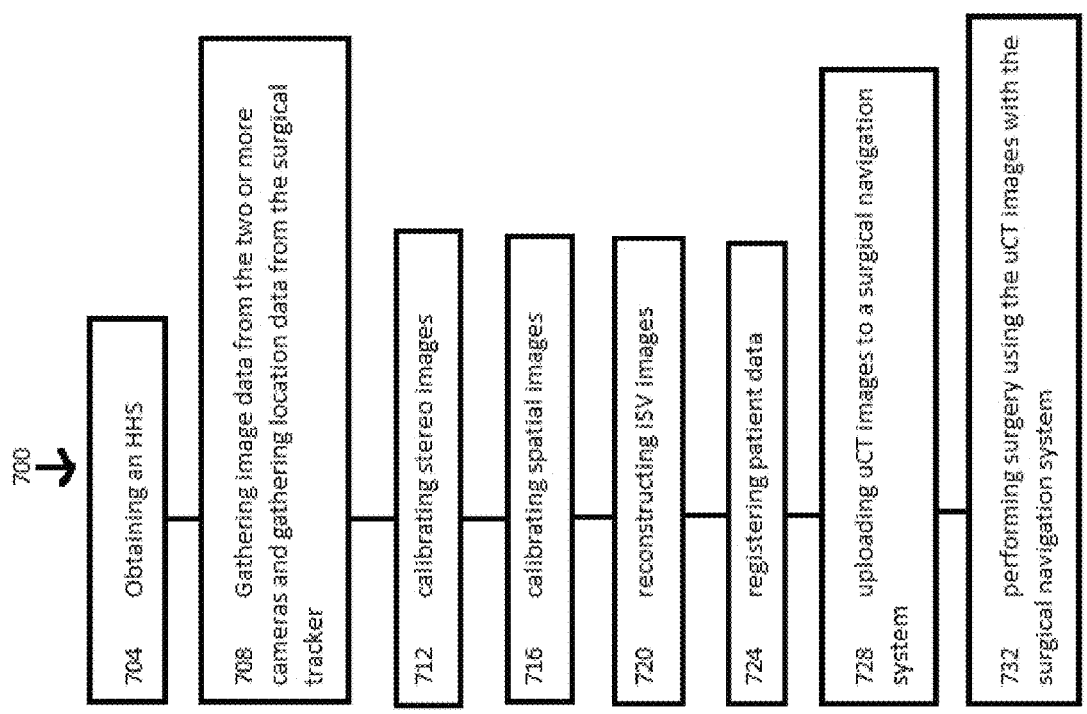
FIG. 7 is a flow chart showing an exemplary method of using a hand-held stereovision system for image updating in surgery.

FIG. 7 is a flow chart showing an exemplary method of using a hand-held stereovision system for image updating in surgery. A method 700 of using a HHS can include obtaining at step 704 an HHS having two or more cameras and a surgical tracker. At step 708, image data can be gathered from the two or more cameras on the HHS, and at the same time, location data can be gathered from the surgical tracker. Gathering image data and location data can include moving the HHS to increase the area of analysis. Moving the HHS to increase the area of analysis can include moving the HHS above and along the spinal region to increase the length of the spinal area being analyzed. At step 712 the stereo images can be calibrated. At step 716 the calibrated stereo images can be calibrated with the spatial data. At step 720 the iSV images can be reconstructed. At 724, the iSV surfaces can be registered with pCT to generate uCT images. At step 728 the uCT images can be uploaded to a surgical navigation system, and at step 732 the uCT images can be used in conjunction with the surgical navigation system to guide and inform a surgeon performing surgery resulting in improved surgical outcomes.

II. Further Considerations

An easy-to-use, radiation-free, accurate, reliable, and automatic spinal registration system and method is provided herein. Surgical navigation is a rapidly evolving field, continually creating new tools to help surgeons improve the safety and efficiency of technically complex procedures.

The system and method can combine multiple true 3D ultrasound volumes efficiently into a single volume for subsequent processing, registration of 3D ultrasound with preoperative MR directly without (free-of) relying upon fiducials in image-guided neurosurgery, and perform multi-threaded registration based on correlation ratio to register 3D ultrasound and preoperative MR images efficiently and accurately. Preliminary experiments with manual methods of intraoperative stereovision (iSV) registration are promising.

The following list summarizes innovations developed for manual iSV approach that are refined to automate registration in the present system and method:
(1) Flow-based registration between two rectified iSV images to derive a full-field, pixel level horizontal disparity map for accurate stereovision reconstruction with vertical flow field to assess fidelity and surface reconstruction quality;
(2) Accurate reconstruction of surgical surfaces from iSV captured at arbitrary zoom and focus based on a single pre-calibration, which significantly increases the flexibility and utility of iSV in the OR;
(3) A simple template-based approach to automatically identify and segment vertebral bodies in the lumbar region via registration;
(4) Verified conformity between the invasive fiducials and intraoperative CT as a registration benchmark to assess the registration accuracy obtained from iSV;
(5) A two-step registration between iSV and preoperative CT to obtain an individual vertebral level registration and creation of registration-updated CT for navigation on a live pig.

The following list summarizes innovations developed for manual iSV approach that are refined for the system and method. More particularly, the system and method can employ methods that use depth-of-field data from stereovision images acquired unobtrusively during surgery to provide simple, automatic, radiation-free surgical navigation. This technology can provide surgeons the ability to quickly update surgical field registration as often as necessary due to changes in spinal alignment, without exposing patients or the surgical team to ionizing radiation. Techniques are employed herein that can utilize spinal geometrical features via a non-linear principal component analysis (NLPCA) for geometrical rectification and deep-learning techniques to completely eliminate the need for manual processing. Algorithms can be employed that perform geometric rectification and transform 2D height maps to identify individual vertebral bodies, compensating for intervertebral motion through Lie-group constrained optimization.

The system and method can be used in the clinical setting of patients with symptomatic lumbar degenerative spondylolisthesis. The system and method provides a portable iSV scanner and associated iSV registration algorithms to adjust for changes in spinal alignment. The system and method can overcome factors in live surgery that interfere with patient registration performance, including bleeding and fluid pooling in the surgical field, movement due to respiration and tissue retraction, and changes in vertebral alignment during the surgical procedure. The system and method can lead to improved accuracy, processing time, surgical and anesthesia time, and implanted screw placements, among others, for iSV guidance versus prior art commercial spinal navigation systems. The iSV methods can be used in open lumbar fusions for degenerative spondylolisthesis in the presence of advanced degenerative changes that alter the native anatomic structure of the vertebral column. The iSV can perform better for larger spinal exposures, and can be used in, by way of non-limiting example, short-segment fusion (3 vertebrae) and multi-level fusion (6 vertebrae).

The present system and method can outperform the prior art in system performance metrics (accuracy and repeatability in measuring point location, and location and orientation of a frame within a coordinate system computation time, registration time), surgical procedure success (position of pedicle screws), and surgical workflow impact (anesthesia time, surgical time, disruption of surgeon, assistant and staff routines). The system and method described herein also outperforms the prior art in the primary outcome of accuracy of registration measured by Target Registration Error (TRE). The system and method can achieve TRE <2 mm. The system and method described herein also outperforms the prior art in secondary outcomes such as Surface to Surface Distance Error (SDE) and surgical procedure success measures of frequency and extent of cortical bone breach by pedicle screws, both as quantitative measurements on post-operative CT images and photographs of sectioned specimens and qualitative ratings by expert surgeons.

Provided herein is a portable, hand-held iSV scanner and software system for efficient (≤10 minutes) and accurate (≤2 mm TRE) intraoperative spine registration. The prior art assumed a rigid spine and used manual methods for iSV data acquired through a surgical microscope. In a significant improvement over the prior art, this system and method can acquire images with a portable camera, automate the registration algorithms, and account for spine flexibility.

Hand Held System

The portable iSV camera can be a standalone, handheld stereovision system that can meet the specific needs in spinal surgery. The present system and method can allow a wider field of view than could be accomplished using prior art systems, because the present system can allow for multiple image sets to be taken from multiple positions to extend the field of view. If multiple iSV image pairs are necessary to capture the exposed spinal surfaces (e.g., to address line-of-sight limitations or to account for multiple vertebral segments in a large exposure), the acquired image acquisitions can be combined prior to subsequent processing. This task can be accomplished by transforming each reconstructed iSV surface into a common coordinate system directly by using the tracking information, or by using an arbitrary acquisition as the reference while stitching the remaining reconstructed iSV surfaces via feature matching between overlapping regions. A unified surface corresponding to the fully exposed vertebrae can be registered with pCT as a single rigid body and further re-registered to compensate for intervertebral motion in subsequent processing. The system and method can be used in hand-held operation to allow for a wider area of view when compared to a stationary system, similarly to tracked intraoperative ultrasound, as a first practical easy to use configuration that can be used easily by surgeons. The advantages of this approach include on-demand availability of the iSV unit for repeated image acquisition during a case (e.g., if the registration is to be updated), full control of the device by the surgeon with little, if any disruption to surgical workflow or need to move equipment in/out of place to make a recording, and familiarity of use/function with similar hand-held intraoperative tools.

The handheld system is very low in cost, is easily calibrated, and incorporates passive (wireless) tracking fiducials embedded within the handle. The portable HHS unit is an improvement over the iSV system mounted to a surgical microscope, is far more functional for spine surgery, and is lower cost.

The system and method can include synchronization of iSV and tracking data, variations/fluctuations in distance from the iSV cameras to the surgical field from intended and unintended hand motion during image recording, and image distortions caused by a sterile cover.

In an alternate configuration, a fixed iSV camera system can be provided, mounted to a stand that can be moved into place and over the surgical field for image acquisition. This approach can be appealing because of its technical simplicity—iSV cameras are stationary, held a fixed and known distance to the surgical field, and may not involve a sterile bag depending on camera mounting distance—but is likely to be more cumbersome in the OR because larger, more bulky equipment would need to be moved into and out of the way during surgery. Another alternate configuration can use a commercial hand-held or mounted scanner to acquire iSV surfaces. However, these devices are relatively expensive and control/flow of the native image data for subsequent processing is less direct If multiple iSV image pairs of the exposed spine are captured by the hand held system (e.g., to address line-of-sight limitations or to account for multiple vertebral segments in a large exposure, or to accommodate hand-swept iSV data acquisition, or data redundancy, etc.), the acquired images will be combined prior to subsequent processing. This task is straightforward, e.g., by transforming each reconstructed iSV surface into a common coordinate system directly by applying the tracking information, or by using an arbitrary acquisition as the reference while stitching the remaining reconstructed iSV surfaces via feature matching between overlapping regions. A unified surface corresponding to the fully exposed vertebrae will be registered with pCT as a single rigid body (and further re-registered to compensate for intervertebral motion in subsequent processing).

iSV Registration Algorithms:

A completely automatic method to perform iSV-to-pCT registration using non-linear principal component and deep learning auto-rectification can be employed to regularize the spine shape and orientation. In the case of a spine (from pCT) image, which can be represented as a chain of segmented vertebrae that deforms cooperatively through rectification, segmentation and parameterization processes, and can be registered to iSV by constrained correspondence mapping, an updated CT (uCT) can be produced for surgical navigation. By capturing changes in spine pose intraoperatively with iSV (from surgical positioning relative to pre-procedure imaging), and determining the correspondences between individual vertebra and their pCT counterparts, a registration pipeline eliminates the need for iCT (or repeated fluoroscopy) by deforming pCT into a coregistered uCT with image guidance accuracy comparable to iCT. The process is repeatable, and the coregistration can be updated during surgery by generating a new uCT from another iSV acquisition later in the case and on-demand, if/when concerns about the accuracy of uCT correspondence with the current surgical field arise. This rectification process is numerically invertible. Therefore, the point correspondences between iSV and pCT in their rectified states can be directly converted into point correspondences expressed in their original coordinates to determine the iSV-to-pCT registration. The pCT and iSV depth maps can encode the same spinal geometrical features (i.e., "height" of the exposed vertebral surface in the posterior-anterior direction). Therefore, they can be directly registered by matching their dense feature maps by maximizing their correlation. The resulting point-to-point correspondences between the depth maps can be used to directly determine their registration in 3D space.

Rectification:

The starting point for iSV to pCT coregistration can be shape rectification of the pCT spine into a neutral posture through nonlinear principal component analysis (NLPCA). NLPCA statistically fits data observations from a non-linear distribution with a set of curved principal surfaces. The present system and method can identify longitudinal and cross-sectional axes of the pCT spine via NLPCA (implemented as a stacked auto-encoder neural network, and flattening these surfaces (by representing them as evenly sampled surface meshes and mapping this data to a set of equal-sized planar Cartesian grids). Depth projection images can also be generated to encode dorsal-ventral surface topology and create one-to-one maps between points in the 2D depth projection image and the 3D rectified spine surface which can simplify and automate segmentation of individual vertebra. Intervertebral boundaries can be identified via Hough line detection, and bony areas between adjacent horizontal lines can act as initial segmentations that can be refined by height thresholding (e.g. to extract detailed structures such as inferior-articular processes and laminae). Resulting labels (in 2D) can be mapped into 3D via the pixel-to-point correspondences between the 2D depth images and the 3D spine surface. Segmented vertebrae can be parameterized by Lie group rotational matrices to model intervertebral motion as differentiable group actions designed to achieve smooth transitions between the individual, rigidly-registered vertebra. To account for posture changes in the pCT relative iSV spine images, constrained minimization can penalize pose changes between adjacent vertebra through the Lie group rotational transform to retain structural integrity.

While the spine is a multi-segment rigid-body, allowing free motion of vertebrae during registration does not ensure anatomically realistic vertebral orientations. The system and method can overcome deficiencies in the prior art by including formulation of individual vertebral registration as a constrained optimization using a Lie group 3D rotation, SO(3), to compensate for intervertebral motion. This method can operate on extracted spine shapes, which enables registration between images and geometrical entities (e.g., pCT-iSV), and is a significant advancement over conventional intensity-based methods that are limited to image volumes. First, the pose of each segmented vertebra can be parameterized into a 3×3 rotational matrix relative to a global reference, chosen to be the rectified vertebra pose. Pose change can then be formulated and regularized using the differentiable actions of SO(3), as before. The rotation transform of the i-th vertebra (from the rectified pose to the original pose) can be formulated as a $G_i \in SO(3)$. For points on the reference and target 3D spine surface, p(m,n) and q(m,n), respectively, where m and n are the pixel location in the depth images, the constrained spine registration can be formulated as minimizing the following objective function:

$$F(G_1, \ldots, G_L, t_1, \ldots, t_L) = \sum_{i \in [1,\ldots,L-1]} \sum_{m,n} \|p(m,n) - G_i q(m,n) - t_i\|^2 \rho_i(m,n) + \frac{\lambda}{2} \sum_{i \in [1,\ldots,L-1]} \|G_i^{-1} G_{i+1} - I\|_F^2 \quad (1)$$

where L is the number of vertebrae, $t_i \in R^3$ is a translation vector, $\rho_i$ is effectively an image mask indicating if pixel (m, n) is part of the i-th segmented vertebra (i.e., 0 or 1), $\lambda > 0$ is a penalty term, and I is an identity matrix. The penalty term, $G_i^{-1} G_{i+1}$, describes the relative pose change between two adjacent vertebrae, i-th and (i+1)-st. This formulation penalizes large relative pose changes and ensures smooth transition between poses. Once $G_i$ and $t_i$ are obtained to minimize F, the 3D warping displacement can also become available to generate registration-updated CT (uCT) via pCT image volume resampling, analogously to model-updated MR for the brain. This scheme can ensure vertebral local rigidity because $G_i$ and $t_i$ are identical for the same vertebra. Conflict around intervertebral boundaries between adjacent vertebrae is efficiently resolved by local smoothing (e.g., via an 11×11×11 3D box filtering) to remove artifacts.

Method for Vertebral Segmentation:

An efficient vertebral segmentation from pCT can help to limit the region of interest (ROI) to register at the level of individual vertebra. First, a typical vertebra can be semi-automatically segmented (e.g., L1; by retaining the image volume between two planes traversing the adjacent intervertebral disks with further manual refinement) to serve as a template. Next, the template and whole-spine volumes can serve as moving and fixed images, respectively, to launch a rigid, affine, and then nonrigid, registration to match the adjacent vertebra (e.g., L2). With an initial starting point, a successful intra-modality registration can be expected. The matched adjacent vertebra (which will be more similar in size and shape) can, in turn, be used as a new template to register and identify the next adjacent vertebra (e.g., L3) with the same process. The system and method can automate and optimize the vertebral segmentation and constrained registration methods described above. First, spinous and inferior articular processes can be identified by detecting local maxima in image intensity (i.e., topological height). Adjacent vertebrae can then be partitioned by tracing contours around the spinous/articular processes. 2D segmentation labels can be mapped to 3D through the one-to-one pixel-point correspondence between the depth images and 3D spine surface to fully segment the vertebrae without requiring accurate segmentation of the facet joints between two adjacent vertebra.

Method for Individual Vertebral Registration:

The spine can be considered as a multi-segment rigid-body. After each vertebral body is identified and paired between pCT and iCT, each pair can then be aligned separately. Allowing free motion of vertebrae during registration does not ensure anatomically realistic vertebral orientations. Biomechanical constraints can be introduced based on established kinematic data. The resulting "correction" can be used to generate uCT by resampling the pCT image volume analogously to model-updated MR for the brain.

Method for Identifying Spinal Level:

A manual process can be used for identifying vertebral level based on unique sequence spinous process tip to transverse process tip distances for each vertebral level, using a graphical user interface (GUI) for visualization and measurement purposes. For each patient case, the CT image stack can be loaded and the bone surface can be segmented using thresholding, and a technician can save points as their 3D coordinates in the image space. The software can calculate the distance points. The computations can be automated to identify lumbar levels during iSV registration.

Computational Efficiency:

The system and method can increase computational throughput with optimized and GPU accelerated algorithms. First, the system and method can incorporate GPU-based acceleration in iSV surface calculation. A dense stereo correspondence algorithm can be implemented, which can be optimized and coded for GPU execution. A previous CPU-based algorithm completed the task in ~80 seconds. Reduction in computational time of the optimized GPU algorithm allowed quadrupling of the number of solver iterations, implementing a two-way correspondence error check, and still completing the process in approximately 0.66 seconds. In terms of computational efficiency, NLPCA spine shape rectification is the most time consuming component. The illustrative processing pipeline currently requires 10-15 minutes to execute. Fortunately, computationally intensive NLPCA analyses involve pCT data and can be computed prior to surgery, and the constrained registration and uCT generation tasks which must occur in the OR can already be executed in 1-2 minutes.

Results:

TRE accuracy ≤2 mm with processing times ≤10 minutes can be achieved with the present system and method, even in the presence of the significant spine posture changes. The system and method can also realize a low-cost hand-held or mounted iSV image acquisition system that is more accurate than the current iSV platform, which is mounted to an operating microscope and used to generate the preliminary results presented here (tracking accuracy ≤0.5 mm, calibration accuracy ≤0.5 mm, reconstructed surface accuracy ≤1 mm) and can accelerate the accompanying image processing algorithms for 3D surface reconstruction to sub-second compute times.

Alternate Embodiments:

The geometrical complexity of spinal processes can introduce errors, and misclassifications that confound approaches. In problems arise during development and operation, other data mining strategies, such as machine learning, deep learning and support vector machine clustering techniques to facilitate feature extraction, identification, and correspondence matching, can be employed to supplement the above-described approaches and algorithms. These methods can also increase the computational costs, in which parallel and/or GPU computing can be applied to maintain processing times required for surgery. Data from the handheld iSV scanner is better than the iSV system mounted to a surgical microscope.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A stereoscopic vision system for use in surgery procedures comprising:
 a handheld stereovision (HHS) device comprising:
  a body;
  at least two cameras mounted to the body, the at least two cameras angled towards a center of a field of view, and having an overlapping region of view;
  a surgical tracker; and
  a data connection to a processor that registers intraoperative stereovision surfaces (iSV) of vertebrae in the overlapping region of view with preoperative CT data by referencing a model of intervertebral motion that (i) maintains anatomically realistic vertebral orientations by modeling the intervertebral motion of segmented vertebrae parameterized for Lie group rotational transformation, and (ii) achieves smooth transitions between individual vertebra by constraining pose changes of the segmented vertebrae for adjacent parameterized vertebra through constrained optimization of the pose changes for the Lie group rotational transformation.

2. The stereoscopic vision system of claim 1 wherein the processor is operatively connected to the handheld stereovision device through the data connection, the processor comprising:
   an image data gathering module; and
   a tracking data gathering module.

3. The stereoscopic vision system of claim 2, the processor further comprising:
   a stereo calibration module; and
   a spatial calibration module.

4. The stereoscopic vision system of claim 2, the processor further comprising an iSV reconstruction module.

5. The stereoscopic vision system of claim 2, the processor further comprising a patient registration module.

6. The stereoscopic vision system of claim 2, further comprising a surgical navigation system.

7. The stereoscopic vision system of claim 6, further comprising an external monitor display system or heads-up display within the surgeon's field of view.

8. A method of performing surgery using a handheld stereovision system, the method comprising:
   obtaining a handheld stereovision (HHS) device, the HHS device including at least two cameras and a surgical tracker;
   gathering image information from the two or more cameras and location data from the surgical tracker at the same time;
   reconstructing iSV images;
   registering patient data with the reconstructed (iSV) images by referencing a model of intervertebral motion that: (i) maintains anatomically realistic vertebral orientations by modeling the intervertebral motion of segmented vertebrae in the images parameterized for Lie group rotational information, and (ii) achieves smooth transitions between individual vertebra by constraining pose changes of the segmented vertebrae for adjacent parameterized vertebra through constrained optimization of the pose changes for the Lie group rotational transformation;
   uploading the registered iSV images as uCT images to a surgical navigation system; and
   performing a surgery in a surgery treatment area using the uCT images with the surgical navigation system.

9. The method of claim 8, further comprising:
   calibrating stereo images; and
   calibrating spatial images.

10. The method of claim 8, wherein the surgery treatment area is a lumbar region of the vertebra.

11. The method of claim 8, further comprising moving the HHS by hand over the surgery treatment area to increase a size of an area being analyzed for surgery.

12. An apparatus for using data from a handheld stereoscopic (HHS) device to assist with surgery comprising:
   a computer system; and
   computer code in the computer system, the computer code comprising:
      a method for gathering image information from two or more cameras on the HHS;
      a method for gathering location information from a tracker on the HHS;
      a method for reconstructing iSV images;
      a method for registering patient data with the reconstructed (iSV) images by referencing a model of intervertebral motion of the vertebrae that: (i) maintains anatomically realistic vertebral orientations by modeling the intervertebral motion of segmented vertebrae parameterized for Lie group rotational transformation, and (ii) achieves smooth transitions between individual vertebra by constraining pose changes of the segmented vertebrae for between adjacent parameterized vertebra through constrained optimization of the pose changes for the Lie group rotational transformation; and
      a method for uploading the registered iSV images as uCT images to a surgical navigation system.

13. The apparatus of claim 12, wherein the computer code further comprises a method for displaying the uCT images to a surgeon during surgery to improve surgical outcomes.

14. The apparatus of claim 12, wherein the computer code further comprises:
   a method of calibrating stereo images; and
   a method of calibrating spatial images.

* * * * *